US012753424B2

(12) United States Patent
Zhang et al.

(10) Patent No.: US 12,753,424 B2
(45) Date of Patent: Oct. 6, 2026

(54) GENETICALLY ENGINEERED MICROORGANISM WITH HIGH YIELD OF L-ISOLEUCINE AND METHOD FOR PRODUCING L-ISOLEUCINE BY FERMENTATION

(71) Applicant: MINT BIOTECHNOLOGIES CO., LTD., Hangzhou (CN)

(72) Inventors: Kechun Zhang, Hangzhou (CN); Jingyu Wang, Hangzhou (CN); Jilong Wang, Hangzhou (CN)

(73) Assignee: MINT BIOTECHNOLOGIES CO., LTD., Hangzhou (CN)

( * ) Notice: Subject to any disclaimer, the term of this patent is extended or adjusted under 35 U.S.C. 154(b) by 327 days.

(21) Appl. No.: 18/561,867

(22) PCT Filed: May 17, 2022

(86) PCT No.: PCT/CN2022/093294

§ 371 (c)(1),
(2) Date: Nov. 17, 2023

(87) PCT Pub. No.: WO2022/242637

PCT Pub. Date: Nov. 24, 2022

(65) Prior Publication Data

US 2024/0240214 A1 Jul. 18, 2024

(30) Foreign Application Priority Data

May 18, 2021 (CN) ........................ 202110541768.X
Jan. 18, 2022 (CN) ........................ 202210053891.1

(51) Int. Cl.

| | |
|---|---|
| ***C12P 13/06*** | (2006.01) |
| ***C12N 9/10*** | (2006.01) |
| ***C12N 9/88*** | (2006.01) |
| ***C12R 1/07*** | (2006.01) |
| ***C12R 1/15*** | (2006.01) |
| ***C12R 1/19*** | (2006.01) |
| ***C12R 1/465*** | (2006.01) |

(52) U.S. Cl.

CPC ............ *C12P 13/06* (2013.01); *C12N 9/1022* (2013.01); *C12N 9/88* (2013.01); *C12R 2001/07* (2021.05); *C12R 2001/15* (2021.05); *C12R 2001/19* (2021.05); *C12R 2001/465* (2021.05); *C12Y 202/01006* (2013.01); *C12Y 403/01019* (2013.01)

(58) Field of Classification Search

None

See application file for complete search history.

(56) References Cited

FOREIGN PATENT DOCUMENTS

| | | | |
|---|---|---|---|
| CN | 1117524 | A | 2/1996 |
| CN | 109554324 | A | 4/2019 |
| CN | 110305829 | A | 10/2019 |
| CN | 114410701 | A | 4/2022 |

OTHER PUBLICATIONS

Elisakova et al., Feedback-Resistant Acetohydroxy Acid Synthase Increases Valine Production in Corynebacterium glutamicum, Appl. Environ. Microbiol. 71, 2005, 207-13. (Year: 2005).*

Uniprot, Accession No. A0A3LOVW79, 2020, www.uniprot.org. (Year: 2020).*

Park et al., Rational Design of *Escherichia coli* for L-Isoleucine Production, ACS Synthetic Biology, 1, 2012, 534-40. (Year: 2012).*

Uniprot, Accession No. P04968, 2020, www.uniprot.org. (Year: 2020).*

Zou et al., Pathway construction and metabolic engineering for fermentative production of β-alanine in *Escherichia coli*, Appl. Microbiol. Biotechnology, 104, 2020, 2545-59. (Year: 2020).*

Zhong et al., Metabolic Engineering of a Homoserine-Derived Non-Natural Pathway for the De Novo Production of 1,3-Propanediol from Glucose, ACS Synth. Biol. 8, 2019, 587-95. (Year: 2019).*

Katsube et al., L-Alanine Exporter, AlaE, of *Escherichia coli* Functions as a Safety Valve to Enhance Survival under Feast Conditions, Int. J. Molecular Sci. 20, 2019, 4942. (Year: 2019).*

Wang et al., Production of L-valine from metabolically engineered Corynebacterium glutamicum, Appl. Microbiol. Biotechnol. 102, 2018, 4319-30. (Year: 2018).*

Yin, Lianghong et al., "Co-expression of feedback-resistant threonine dehydratase and acetohydroxy acid synthase increase L-isoleucine production in Corynebacterium glutamicum", Metabolic Engineering, vol. 15, Jul. 4, 2012; pp. 542-550.

Chen, Lin; Rational design and reengineering of allosteric regulation of threonine deaminase from *Escherichia coli*; Full-text database of China's outstanding doctoral and master's degree theses (Master's degree); vol. , No. 05, May 15, 2013;pp. 1-77.

Park, Jin Hwan et al., "Rational Design of *Escherichia coli* for L-Isoleucine Production", ACS Synth. Biol.; Sep. 7, 2012; pp. 532-540.

Park, Jin Hwan Park et al., "Fermentative production of branched chain amino acids: a focus on metabolic engineering", Applied Microbiology and Technology, vol. 85, No. 3, Oct. 21, 2009, pp. 491-506.

Yu, Shengzhu et al., "Metabolic engineering of Corynebacterium glutamicum for producing branched chain amino acids", Microbial Cell Factories, vol. 20, No. 1, Dec. 1, 2021, pp. 1-14.

* cited by examiner

*Primary Examiner* — Todd M Epstein
(74) *Attorney, Agent, or Firm* — NKL Law; Allen Xue

(57) ABSTRACT

A method for producing L-isoleucine at a higher yield by fermentation includes the step of using a genetic engineering method to obtain a genetically engineered strain. The genetically engineered strain has a threonine deaminase gene substantially releasing the inhibition of L-isoleucine and/or an acetylated hydroxy acid synthetase III gene substantially releasing the inhibition of L-isoleucine; and performing fermentation culture on the genetically engineered strain, adding diketobutyric acid or a raw material capable of being converted into diketobutyric acid in a culture process, and separating L-isoleucine from a culture after the end of culturing. Further provided is a genetically engineered strain for realizing high yield of L-isoleucine.

2 Claims, No Drawings

GENETICALLY ENGINEERED MICROORGANISM WITH HIGH YIELD OF L-ISOLEUCINE AND METHOD FOR PRODUCING L-ISOLEUCINE BY FERMENTATION

TECHNICAL FIELD

The present disclosure relates to the field of biochemical engineering, and in particular to a genetically engineered microorganism with high L-isoleucine yield and a method for producing L-isoleucine by fermentation of the microorganism.

BACKGROUND

L-isoleucine, or isoleucine, is a branched-chain amino acid (BCAA) and one of the eight essential amino acids that can not be synthesized in humans and animals and must be supplied by external sources. It has various physiological functions, and is a starting material for the synthesis of human hormones and enzymes for promoting protein production and inhibiting protein decomposition. L-isoleucine plays an important role in human life activities, thereby having a wide range of applications and high commercial value in food and pharmaceutical industries.

There are three methods for producing L-isoleucine, i.e., extraction, chemical synthesis and fermentation. Currently, only fermentation method is implemented in industrial production. Fermentation is a process of biosynthesis and excessive accumulation of L-isoleucine utilizing the metabolism of microorganisms, and includes two types, i.e., precursor-adding fermentation and direct fermentation. The precursor-adding fermentation is also known as microorganism transformation. In this method, glucose is used as carbon source and energy source for fermentation, a specific precursor is added to avoid the feedback regulation in the biosynthetic pathway of amino acids and is then effectively transformed into the target amino acid through the action of the microorganism. For L-isoleucine, the precursor mainly includes α-aminobutyric acid, α-hydroxybutyric acid, α-ketobutyric acid, D-threonine, etc., and the microorganism used mainly includes *Bacillus, Pseudomonas, Serratia marcescens*, etc. With the aid of the ability of microorganisms to synthesize required amino acids, the direct fermentation can breed auxotroph strains or amino acid structure analog-resistant mutant strains obtained by mutagenic treatment of specific microorganisms, so as to relieve the feedback inhibition and repression in the metabolism regulation and achieve the goal of excessively accumulating a certain amino acid. Most of the current L-isoleucine-producing microorganisms are obtained by mutation breeding of glutamic acid-producing microorganisms (e.g., *Brevibacterium flavum, Corynebacterium glutamicum*, and *Brevibacterium lactofermentum*, etc.).

At present, a plurality of enterprises are producing L-isoleucine by fermentation in China, but there are still problems such as low acid production, poor extraction of fermentation products and the like. Therefore, improving the fermentation microorganisms and technical process of L-isoleucine, increasing the acid production and reducing the difficulty of extraction, are of great importance to improve the yield and market competitiveness of L-isoleucine in China.

SUMMARY

The present disclosure is intended to provide a novel genetically engineered microorganism, and a method for achieving high L-isoleucine yield by culturing the genetically engineered microorganism in a culture medium containing threonine.

The *Escherichia* species having L-isoleucine-producing ability provided herein is characterized by comprising an ilvA mutant gene reliving feedback-inhibition of L-isoleucine encoding threonine deaminase substantially resistant to feedback-inhibition of L-isoleucine or a threonine dehydratase tdcB gene and comprising a mutant of (ilvIH, ilvBN, ilvGM or alsS) gene reliving feedback-inhibition of L-isoleucine encoding acetohydroxy acid synthase substantially resistant to feedback-inhibition of L-isoleucine, as well as isoleucine transporter tdcC, thereby achieving sufficient supply of precursor 2-oxobutyric acid required by the synthesis of isoleucine.

Inside cell, isoleucine is synthesized from 2-oxobutyric acid and pyruvate by catalysis of acetohydroxy acid isomeroreductase (ilvC), dihydroxy-acid dehydratase (ilvD) and branched-chain amino acid aminotransferase (ilvE)/branched-chain amino acid dehydrogenase (leuDH), and then transported out of the cell by the branched-chain amino acid exporter ygaZH or brnEF. Among these, ilvC may be a wild-type ilvC or a mutated version ilvCm, and the above genes may be maintained on non-chromosomal DNA or chromosomal DNA.

The present disclosure further provides a method for producing L-isoleucine by fermentation, wherein the method comprises adding threonine to a culture medium, culturing the *Escherichia* species described above to allow accumulation of L-isoleucine in the cultures, and then extracting L-isoleucine from the cultures.

DETAILED DESCRIPTION

I. Definitions

In the present disclosure, unless otherwise indicated, scientific and technical terms have the same meaning as commonly understood by those skilled in the art. In addition, the terms and laboratory procedures related to nucleic acid chemistry, molecular biology, cell and tissue culture, microbiology and immunology used herein are the terms and conventional procedures widely used in the corresponding fields. Also, in order to better understand the present invention, the definitions and interpretations of the related terms are provided below.

It should be appreciated that the terms used herein are for the purpose of illustrating particular embodiments only, and are not intended to be limiting. The articles "a", "an" and "the" are used herein to refer to one or more than one of the grammatical object of the article. The use of alternatives (e.g., "or") should be understood to refer to one, two, or any combination of the alternatives. The term "and/or" should be interpreted as referring to one or both of the alternatives. As used herein and unless otherwise specified, when the term "about" modifies a measurable value such as an amount, a period of time, etc., it refers to a variation of +10%, preferably +5%, more preferably +1% and even more preferably +0.1% from the given value, so long as such variation is suitable for implementing the method disclosed herein. As used herein, the term "gene synthesis" refers to a generation process using recombinant DNA techniques or a production process using DNA or amino acid sequence synthesis techniques available and well known in the art. The term "encode" or "code" refers to the inherent property of specific sequences of nucleotides in a polynucleotide, such as a gene, a cDNA, or an mRNA, to serve as a template in synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of an mRNA corresponding to the gene produces the protein in a cell or other biological system. Both the coding strand, which comprises a nucleotide sequence equivalent to the mRNA sequence and is usually provided in a sequence listing, and the non-coding strand, which is used as a template for transcription of a gene or cDNA, may be referred to as encoding the protein or other product of that gene or cDNA.

As used herein, the term "endogenous" refers to any substance derived from or produced within an organism, cell, tissue or system.

As used herein, the term "exogenous" refers to any substance introduced into or produced outside of an organism, cell, tissue or system.

As used herein, the term "expression" is defined as the transcription and/or translation of a particular nucleotide sequence driven by its promoter.

As used herein, the term "nucleic acid construct" refers to a vector of a recombinant polynucleotide comprising an expression control sequence operably linked to a nucleotide sequence to be expressed. The nucleic acid construct comprises sufficient cis-regulatory elements for expression, and other elements for expression may be supplied by the host cell or an in vitro expression system. Nucleic acid constructs include all those known in the art, such as cosmids, plasmids (e.g., naked or contained in liposomes) and viruses (e.g., lentiviruses, retroviruses, adenoviruses and adeno-associated viruses) incorporated into recombinant polynucleotides.

Unless otherwise specified, the "polynucleotide sequence encoding an amino acid sequence" includes all nucleotide sequences that are degenerate versions of each other and encode the same amino acid sequence. The phrase "nucleotide sequence encoding a protein or an RNA" may also include introns to the extent that the nucleotide sequence encoding the protein may contain an intron(s) in some versions.

As used herein, the term "operably linked" refers to a functional linkage between a regulatory sequence and a heterologous nucleic acid sequence that results in expression of the latter. For example, a first nucleic acid sequence is operably linked to a second nucleic acid sequence when the first nucleic acid sequence is in a functional relationship with the second nucleic acid sequence. For instance, a promoter is operably linked to a coding sequence if the promoter affects the transcription or expression of the coding sequence. Generally, operably linked DNA sequences are contiguous, wherein two protein-encoding regions are necessarily linked in the same reading frame. The term "polynucleotide" as used herein is defined as a nucleotide chain. In addition, nucleic acid is a polymer of nucleotides. Thus, the terms "nucleic acid" and "polynucleotide" as used herein are interchangeable. Those skilled in the art has general knowledge that nucleic acids are polynucleotides that can be hydrolyzed into monomeric "nucleotides". Monomeric nucleotides can be hydrolyzed into nucleosides. As used herein, polynucleotides include, but are not limited to, all nucleic acid sequences obtained by any means available in the art, including, but not limited to, recombinant means (i.e., cloning of nucleic acid sequences from a recombinant library or cell genome using common cloning techniques, PCR™ and the like) and synthetic means.

In various illustrative embodiments, the polynucleotides contemplated herein include, but are not limited to, polynucleotides comprising expression vectors, virus vectors, transfer plasmids and expression cassettes, and polynucleotides encoding polypeptides of cytokine antibodies or antibody fragments or antigen-binding fragments.

As disclosed elsewhere herein or as known in the art, the polynucleotides, regardless of the length of the coding sequence itself, may be combined with other DNA sequences, such as promoters and/or enhancers, untranslated regions (UTRs), polyadenylation signals, additional restriction enzyme cutting sites, multiple cloning sites, internal ribosome entry sites (IRESs), recombinase recognition sites, termination codons, transcription termination signals, post-transcriptional response elements, polynucleotides encoding self-cleaving polypeptides, and epitope tags, such that their overall length may vary remarkably. It is therefore contemplated that a polynucleotide fragment of almost any length can be employed, with the overall length preferably being limited by the ease of preparation and use in the intended recombinant DNA protocol.

As used herein, the term "vector" refers to a composition of matter that comprises an isolated nucleic acid and can be used to deliver the isolated nucleic acid to the interior of a cell. The transferred nucleic acid is typically linked to, e.g., inserted into, a vector nucleic acid molecule. A vector may comprise sequences that direct autonomous replication in the cell, or may comprise sequences sufficient to allow integration into the host cell DNA. Many vectors are known in the art, including but not limited to plasmids, phagemids, artificial chromosomes, bacteriophages and animal viruses. Therefore, the term "vector" encompasses an autonomously replicating plasmid or virus.

Illustrative methods for delivering the polynucleotides contemplated in particular embodiments include, but are not limited to: electroporation, sonoporation, lipofection, microinjection, particle bombardment, virons, liposomes, immunoliposomes, polycation or lipid:nucleic acid conjugates, naked DNA, artificial virons, DEAE-dextran-mediated transfer, gene gun, heat shock and the like.

The "expression control sequences", "control elements" or "regulatory sequences" present in an expression vector are non-translated regions of the vector (i.e., origin of replication, selection cassettes, promoters, enhancers, translational initiation signal introns, post-transcriptional regulatory elements, a polyadenylation sequence, 5' and 3' untranslated regions), which interact with host cell proteins for transcription and translation. The length and specificity of such elements may vary. Depending on the vector system and host utilized, any number of suitable transcription and translation elements, including ubiquitous promoters and inducible promoters may be used. In particular embodiments, the polynucleotide is a vector including, but not limited to, expression vectors and virus vectors, and comprises exogenous, endogenous or heterologous control sequences, such as promoters and/or enhancers. An "endogenous" control sequence is a sequence that is naturally linked with a given gene in the genome. An "exogenous" control sequence is a sequence that is placed in juxtaposition to a gene by genetic manipulation (i.e., molecular biotechnology) such that the transcription of that gene is directed by the linked enhancer/promoter. A "heterologous" control sequence is an exogenous sequence that is from a different species than the cell being genetically manipulated. A "synthetic" control sequence may comprise elements of one or more endogenous and/or exogenous sequences, and/or sequences determined in vitro or in silico that provide optimal promoter and/or enhancer activity for use in a particular gene therapy. As used herein, the term "promoter" refers to a recognition site for a polynucleotide (DNA or RNA) to which an RNA polymerase binds. The RNA polymerase initiates the transcription of the polynucleotides operably linked to the promoter.

The term "enhancer" refers to a segment of DNA containing a sequence that can provide enhanced transcription and in some cases may function independently of its orientation relative to another control sequence. An enhancer can function cooperatively or additively with the promoter and/or another enhancer element. The term "promoter/enhancer" refers to a fragment of DNA that contains a sequence capable of providing the function of both a promoter and an enhancer.

The term "conditional expression" may refer to any type of conditional expression including, but not limited to: inducible expression; repressible expression; expression in cells or tissues with a particular physiological, biological or disease state, etc. This definition is not intended to exclude cell- or tissue-specific expression. Certain embodiments provide conditional expression of a polynucleotide of interest. For example, the expression is controlled by subjecting a cell, tissue, organism and the like to a treatment or condition that causes a polynucleotide to be expressed or that causes an increase or decrease in expression of a polynucleotide encoded by a polynucleotide of interest.

Illustrative examples of inducible promoters/systems include, but are not limited to, steroid-inducible promoters, such as promoters for genes encoding glucocorticoid or estrogen receptors, metallothionein promoter; MX-1 promoter, "GeneSwitch" mifepristone-regulatable system, tetracycline-dependent regulatory system, etc.

In some embodiments, the genetically modified cell comprises a polynucleotide further comprising a positive marker that enables the selection of cells of negative selectable phenotype in vitro. The positive selectable marker may be a gene that, upon being introduced into a host cell, expresses a dominant phenotype that allows for positive selection of cells carrying the gene. Such genes are known in the art.

In one embodiment, the positive selectable marker and the negative selectable marker are linked such that loss of the negative selectable element is also accompanied by loss of the positive selectable marker. In a particular embodiment, the positive and negative selectable markers are fused such that loss of one necessarily leads to loss of the other.

As used herein, the term "transfection" or "transformation" or "transduction" refers to a process by which exogenous nucleic acid is transferred or introduced into a recipient microorganism. A "transfected", "transformed" or "transduced" microorganism is one that has been transfected, transformed or transduced with exogenous nucleic acid. The microorganism includes a primary strain and its progeny. The recipient microorganism may be *Escherichia coli, Corynebacterium glutamicum, Bacillus subtilis, Bacillus megaterium, Vibrio natriegens, Bacillus amyloliquefaciens, Saccharomyces cerevisiae*, or the like.

In the specification of the present disclosure, the ilvA gene encoding threonine deaminase substantially resistant to feedback-inhibition of L-isoleucine is referred to as "ilvA mutant gene reliving L-isoleucine feedback-inhibition", and the ilvIH gene encoding acetohydroxy acid synthase III substantially resistant to feedback-inhibition of L-isoleucine is referred to as "ilvIH mutant gene reliving L-isoleucine feedback-inhibition".

II. Detailed Description

A first aspect of the present disclosure relates to a polynucleotide molecule comprising a gene encoding threonine deaminase substantially resistant to feedback-inhibition of L-isoleucine.

In one embodiment, the gene encoding threonine deaminase substantially resistant to feedback-inhibition of L-isoleucine may be an ilvA mutant gene reliving the feedback-inhibition.

Alternatively, provided is a polynucleotide molecule comprising a gene encoding acetohydroxy acid synthase III substantially resistant to feedback-inhibition of L-isoleucine.

In one embodiment, the gene encoding acetohydroxy acid synthase III substantially resistant to feedback-inhibition of L-isoleucine may be one or more of an ilvIH mutant gene reliving the feedback-inhibition, an ilvBN mutant gene reliving the feedback-inhibition, an L-isoleucine-resistant mutant of ilvGM gene and an alsS mutant gene reliving the feedback-inhibition.

In one specific embodiment, the gene encoding acetohydroxy acid synthase III substantially resistant to feedback-inhibition of L-isoleucine may be an ilvIH mutant gene reliving the feedback-inhibition.

In one embodiment, provided is a polynucleotide molecule, comprising a gene encoding threonine deaminase substantially resistant to feedback-inhibition of L-isoleucine and a gene encoding acetohydroxy acid synthase III substantially resistant to feedback-inhibition of L-isoleucine. The gene encoding threonine deaminase substantially resistant to feedback-inhibition of L-isoleucine and the gene encoding acetohydroxy acid synthase III substantially resistant to feedback-inhibition of L-isoleucine are as defined above.

The ilvA mutant gene reliving L-isoleucine feedback-inhibition described herein is different from a wild-type ilvA gene in that the ilvA mutant gene has a mutation relative to the wild-type ilvA gene, wherein the mutation refers to one that confers resistance to the feedback-inhibition of L-isoleucine on ilvA gene encoding, such as L447F and/or L451A.

The ilvIH mutant gene reliving L-isoleucine feedback-inhibition described herein is different from the wild-type ilvIH gene. The ilvIH mutant gene has a mutation relative to the wild-type ilvIH gene, wherein the mutation refers to one that confers resistance to the feedback-inhibition of L-isoleucine on ilvH gene encoding, such as G14D and/or S17F.

Any of the polynucleotide molecules described above may further comprise one or more of a threonine dehydratase gene (e.g., tdcB gene), a threonine transporter gene (e.g., tdcC gene), an exporter gene (e.g., *E. coli* exporter ygaZH gene and ('. *glutamicum* exporter brnEF gene), an acetohydroxy acid isomeroreductase gene (e.g., ilvC gene), dihydroxy-acid dehydratase (e.g., ilvD gene), branched-chain amino acid aminotransferase (e.g., ilvE gene) and branched-chain amino acid dehydrogenase (e.g., leuDH gene). The gene may be wild-type or mutant gene. For example, in one embodiment, the ilvC gene may be a wild-type ilvC or a mutant ilvGm, wherein the mutant ilvGm refers to a mutant ilvC gene using NADH as a coenzyme, which is different from the wild-type ilvC using NADPH as a coenzyme. The mutant ilvC carries mutations L67E, R68F and K75E.

In one embodiment, the threonine dehydratase (tdcB), dihydroxy-acid dehydratase (ilvD), branched-chain amino acid aminotransferase (ilvE) and branched-chain amino acid exporter ygaZH can be derived from *E. coli* genome.

In one embodiment, the branched-chain amino acid dehydrogenase (leuDH) may be derived from *B. subtilis*. In one embodiment, the branched-chain amino acid exporter (brnEF) may be derived from *C. glutamicum.*

As known to those skilled in the art, the above genes can be obtained by PCR reaction using DNA primers. The threonine transporter gene (tdcC) directly affects the flux of threonine into cells, and the expression intensity thereof can be finely regulated for optimal production of isoleucine. The control of the expression intensity of the threonine transporter gene can be achieved by using promoters of different intensities (e.g., constitutive promoters or inducible promoters), by using inducers of different concentrations (for inducible promoters), or by using different types of plasmids (free from the chromosomes), and by integration at different locations in the genome. Therefore, a second aspect of the present disclosure relates to a vector comprising the polynucleotide molecule according to any one of the preceding items, wherein the vector further comprises common elements including, but not limited to, one or more of an origin of replication (ORI), an antibiotic resistance gene, a multiple cloning site (MCS), a promoter, an enhancer, a primer binding site, and a selectable marker.

In one embodiment, the vector is a plasmid and/or a virus vector. In one embodiment, the plasmid is one or more of pZAlac and pZElac. In one embodiment, the virus vector is one or more of an adenovirus, an adeno-associated virus (AAV), a retrovirus and a lentivirus. A third aspect of the present disclosure relates to a genetically engineered microorganism comprising a gene encoding threonine deaminase substantially resistant to feedback-inhibition of L-isoleucine.

In one embodiment, the gene encoding threonine deaminase substantially resistant to feedback-inhibition of L-isoleucine may be an ilvA mutant gene reliving the feedback-inhibition.

Alternatively, provided is a genetically engineered microorganism comprising a gene encoding acetohydroxy acid synthase III substantially resistant to feedback-inhibition of L-isoleucine.

In one embodiment, the gene encoding acetohydroxy acid synthase III substantially resistant to feedback-inhibition of L-isoleucine may be one or more of an ilvIH mutant gene reliving the feedback-inhibition, an ilvBN mutant gene reliving the feedback-inhibition, an ilvGM gene reliving the feedback-inhibition and an alsS mutant gene reliving the feedback-inhibition.

In one specific embodiment, the gene encoding acetohydroxy acid synthase III substantially resistant to feedback-inhibition of L-isoleucine may be an ilvIH mutant gene reliving the feedback-inhibition.

In one embodiment, provided is a genetically engineered microorganism, comprising a gene encoding threonine deaminase substantially resistant to feedback-inhibition of L-isoleucine and a gene encoding acetohydroxy acid synthase III substantially resistant to feedback-inhibition of L-isoleucine.

In one embodiment, the gene encoding threonine deaminase substantially resistant to feedback-inhibition of L-isoleucine and the gene encoding acetohydroxy acid synthase III substantially resistant to feedback-inhibition of L-isoleucine are as defined above.

In one embodiment, the genetically engineered microorganism is selected from strains from one or more of the following: *E. coli, Bacillus, Corynebacterium, Streptomyces*, yeast, and the like.

As described above, the genes may be inserted into a vector DNA capable of autonomous replication, and then introduced into a host where they may be retained as a plasmid-like extrachromosomal DNA.

Alternatively, the above genes may be encoded into the chromosomes of the host microorganism by using transduction, a translocon, Mu phage, or homologous recombination. For efficient expression of the above genes, other promoters working in microorganisms such as lac, trp, PL, and tac, may be linked. In one embodiment, the activities of lactate dehydrogenase ldhA and alcohol dehydrogenase adhE in the genetically engineered microorganism are separately or simultaneously diminished or eliminated.

In one embodiment, the activity of pyruvate dehydrogenase in the genetically engineered microorganism is diminished or eliminated.

In one embodiment, the genetically engineered microorganism has a 30% or greater increase in acetohydroxy acid synthase activity as compared with a wild-type microorganism.

In one embodiment, the genetically engineered microorganism has a 30% or greater increase in threonine deaminase activity as compared with a wild-type microorganism. In one embodiment, the genetically engineered microorganism comprises any of the polynucleotide molecules and/or the vectors described above. The genetically engineered microorganism disclosed herein has the ability to produce high L-isoleucine yield. A fourth aspect of the present disclosure relates to a method for constructing a genetically engineered microorganism with high L-isoleucine yield, wherein the method comprises construction and expression of plasmids, genomic integration (e.g., homologous recombination mediated by CRISPR, lambda Red, etc.), and the like. A fifth aspect of the present disclosure relates to a composition comprising any of the polynucleotide molecules and/or the vectors described above, or any of the genetically engineered microorganisms described above. A sixth aspect of the present disclosure relates to use of any of the polynucleotide molecules and/or the vectors described above or any of the genetically engineered microorganisms described above in producing L-isoleucine or in preparing a medicament or a health-care food product containing L-isoleucine.

A seventh aspect of the present disclosure relates to a method for producing L-isoleucine, wherein any of the polynucleotide molecules and/or the vectors described above and any of the genetically engineered microorganisms described above are used.

In one embodiment, the method comprises culturing any of the genetically engineered microorganisms described above or for culturing a strain comprising any of the polynucleotide molecules and/or the vectors described above by fermentation.

In one embodiment, the method comprises adding 0.1%-5% threonine to the fermentation culture medium to increase the supply of precursor 2-oxobutyric acid.

In one embodiment, threonine may also be added during a fed-batch fermentation culture, and the concentration of threonine in the feed medium is 10%-14%.

In one embodiment, the method comprises the following steps:

(i) culturing any of the genetically engineered microorganisms described above in a culture condition with insufficient oxygen, and adding 2-oxobutyric acid or a precursor capable of being transformed into 2-oxobutyric acid, such as threonine, fumaric acid, aspartic acid, homoserine, propionic acid and the like; and (ii) isolating the L-isoleucine from the cultures in (i). In one embodiment, the fermentation culture medium of the method comprises glucose at 20 g/L, ammonium sulfate at 8 g/L, yeast extract at 5 g/L, potassium dihydrogen phosphate at 0.8 g/L, manganese sulfate pentahydrate at 0.02 g/L, threonine at 15 g/L, betaine at 1 g/L, serine at 1 g/L, nicotinic acid at 0.01 g/L and VB1 at 0.005 g/L. In one embodiment, the fermentation culture medium of the method comprises glucose at 4%, threonine at 1.5%, serine at 0.1%, yeast extract at 0.5%, $MgSO_4$ at 0.12%, $CaCl_2$) at 0.01%, $NH_4Cl$ at 0.26%, NaCl at 0.05%, $Na_2HPO_4$ at 0.6%, $KH_2PO_4$ at 0.3%, VB1 at 0.0005%, betaine at 0.1%, $MnSO_4 \cdot 5H_2O$ at 0.002% and nicotinic acid at 0.01%.

III. Examples

Example 1. Construction of Recombinant Plasmids pZA-ilvAIH and pZA-tdcBC-ilvIH An ilvA mutant gene reliving L-isoleucine feedback-inhibition and an ilvIH mutant gene reliving L-isoleucine feedback-inhibition were obtained by PCR, then the DNA fragments were digested by restriction endonuclease, and ligated to plasmid pZAlac by T4 ligase to give recombinant plasmid pZA-ilvAIH. Similarly, a tdcB gene, an ilvIH mutant gene reliving L-isoleucine feedback-inhibition fragment and a tdcC gene encoding threonine transporter were obtained by PCR, then digested by restriction endonuclease, and ligated to plasmid pZAlac by ligase to give recombinant plasmid pZA-tdcBC-ilvIH. Finally, these two recombinant plasmids were transformed into ilvD deletion strain (BW25113 background) to give IL1 and IL2, respectively.

Example 2. Preparation of (R)-2,3-dihydroxy-3-methylpentanoate, a precursor of L-isoleucine The strains IL1 and IL2 in Example 1 were used, and the culture medium was a commonly used fermentation culture medium containing: glucose at 4%, threonine at 1%, yeast extract at 0.5%, $MgSO_4$ at 0.12%, $CaCl_2$) at 0.01%, $NH_4Cl$ at 0.1%, NaCl at 0.05%, $Na_2HPO_4$ at 0.6%, $KH_2PO_4$ at 0.3% and VB1 at 0.0005%. The culture medium was adjusted to pH=7.0-7.2 with NaOH and hydrochloric acid, and sterilized at 115° C. for 15 min.

Culture: The strains were seeded into an LB culture medium and cultured at 37° C. for 10 h at a rotation speed of 240 rpm. The LB culture was inoculated at an amount of 4% into the fermentation medium containing kanamycin, and fermented at 30° C. for 60 h in a 125-mL Erlenmeyer flask (medium volume 5 mL, containing 0.3 g of $CaCO_3$) at 240 rpm. 10.2 g/L and 9.5 g/L of 2,3-dihydroxy-3-methylpentanoate were produced by IL1 and IL2, respectively.

Example 3. Screening of Genetically Engineered L-Isoleucine-Producing Microorganism The ilvC/ilvCm, ilvD, ilvE/leuDH and ygaZH/brnEF genes were obtained by PCR, then digested by restriction endonuclease, and ligated to plasmid pZElac through a ligase to give the following recombinant plasmid combinations: pZE-ilvCD-ilvE-ygaZH, pZE-ilvCD-leuDH-ygaZH, pZE-ilvCD-leuDH-brnEF, pZE-ilvCmD-ilvE-ygaZH, pZE-ilvCmD-ilvE-brnEF, pZE-ilvCmD-leuDH-ygaZH and pZE-ilvCmD-leuDH-brnEF.

The above plasmids were transferred into IL1 or IL2 strain with adhE and IdhA deletions to give a series of strains for producing isoleucine by fermentation. 14 strains obtained by the above method were used, and the shake flask fermentation culture medium contained: glucose at 4%, threonine at 1.5%, serine at 0.1%, yeast extract at 0.5%, $MgSO_4$ at 0.12%, $CaCl_2$) at 0.01%, $NH_4Cl$ at 0.26%, NaCl at 0.05%, $Na_2HPO_4$ at 0.6%, $KH_2PO_4$ at 0.3%, VB1 at 0.0005%, betaine at 0.1%, $MnSO_4 \cdot 5H_2O$ at 0.002% and nicotinic acid at 0.01%. The culture medium was adjusted to pH=7.0-7.2 with NaOH and hydrochloric acid, and sterilized at 115° C. for 15 min.

Culture: The strains were seeded into an LB culture medium and cultured at 37° C. for 10 h at a rotation speed of 240 rpm. The LB culture was inoculated at an amount of 4% into a fermentation culture medium containing ampicillin and kanamycin, and cultured at 30° C. for 8 h in a 125-mL Erlenmeyer flask (medium volume 5 mL, containing 0.3 g of $CaCO_3$) at 240 rpm. IPTG was then added to a final concentration of 0.3 mM, and the fermentation was continued for 48 h-60 h and then stopped. The yields of valine and isoleucine are shown in Table 1.

TABLE 1

Results of shake flask fermentation in Example 3

| pZA plasmid | pZE plasmid | Valine (g/L) | Isoleucine (g/L) |
|---|---|---|---|
| pZA-ilvAIH | pZE-ilvCD-ilvE-ygaZH | 4.0 | 11.1 |
| | pZE-ilvCmD-leuDH-ygaZH | 1.3 | 3.7 |
| | pZE-ilvCmD-leuDH-brnEF | 1.4 | 2.1 |
| | pZE-ilvCD-leuDH-ygaZH | 0.0 | 0.0 |
| | pZE-ilvCmD-ilvE-ygaZH | 3.9 | 13.8 |
| | pZE-ilvCD-ilvE-brnEF | 3.1 | 13.3 |
| | pZE-ilvCmD-ilvE-brnEF | 2.6 | 9.4 |
| pZA-tdcBC-ilvIH | pZE-ilvCD-ilvE-ygaZH | 4.3 | 11.1 |
| | pZE-ilvCmD-leuDH-ygaZH | 3.1 | 7.5 |
| | pZE-ilvCmD-leuDH-brnEF | 2.8 | 11.1 |
| | pZE-ilvCD-leuDH-ygaZH | 0.0 | 0.0 |
| | pZE-ilvCmD-ilvE-ygaZH | 3.1 | 8.5 |
| | pZE-ilvCD-ilvE-brnEF | 2.0 | 12.2 |
| | pZE-ilvCmD-ilvE-brnEF | 1.8 | 11.9 |

Example 4. Production of L-Isoleucine by Fermentation with Genetically Engineered Microorganism (Recipient: DV10)

The optimal plasmid combination pZA-ilvAIH and pZE-ilvCmD-ilvE-ygaZH in Example 3 was used and transferred into the recipient strain DV10 (ΔldhA Δpta ΔpoxB ΔadhE ΔpflB ΔmgsA ΔfrdA ΔdadA ΔavtA ΔilvE) for fermenter experiment.

Production: The strain was seeded into an LB culture medium, cultured at 37° C. for 12 h, and then inoculated at an amount of 5% into a 1-L automatic fermenter containing a fermentation culture medium with an appropriate amount of antibiotics (containing glucose at 20 g/L, ammonium sulfate at 8 g/L, yeast extract at 5 g/L, potassium dihydrogen phosphate at 0.8 g/L, manganese sulfate pentahydrate at 0.02 g/L, threonine at 15 g/L, betaine at 1 g/L, serine at 1 g/L, nicotinic acid at 0.01 g/L and VB1 at 0.005 g/L). The temperature of the fermentation broth was controlled in a segmented mode at 37° C. for 0-10 h and 30° C. for 10-40 h. An appropriate amount of air was introduced, and the stirring speed was appropriately adjusted to a constant rotation speed of 800 rpm to control the dissolved oxygen. The pH was controlled at 6.8-7.2 by automatically feeding liquid ammonia, and an appropriate amount of defoamer GPE was fed for defoaming. The residual sugar was controlled below 1% by feeding a 500 g/L glucose solution, while a 90 g/L threonine mother liquor was fed. The fermentation was carried out for 40 h. At the time of discharge, the yield of L-isoleucine was 43.1 g/L, and the conversion rate was 84%.

Example 5. Production of L-Isoleucine by Fermentation (Recipient Cell: CCK19)

The plasmids pZA-ilvAIH and pZE-ilvCmD-ilvE-ygaZH in Example 3 were transformed into strain CCK19 (ΔldhA ΔpoxB ΔadhE ΔaceE ΔfrdBC). Shake flask fermentation culture medium contained: glucose at 4%, threonine at 1.5%, serine at 0.1%, yeast extract at 0.5%, $MgSO_4$ at 0.12%, $CaCl_2$) at 0.01%, $NH_4Cl$ at 0.26%, NaCl at 0.05%, $Na_2HPO_4$ at 0.6%, $KH_2PO_4$ at 0.3%, VB1 at 0.0005%, betaine at 0.1%, $MnSO_4 \cdot 5H_2O$ at 0.002% and nicotinic acid at 0.01%. The culture medium was adjusted to pH=7.0-7.2 with NaOH and hydrochloric acid, and sterilized at 115° C. for 15 min.

Culture: The strains were seeded into an LB culture medium and cultured at 37° C. for 10 h at a rotation speed of 240 rpm. The LB culture was inoculated at an amount of 4% into a fermentation culture medium containing ampicillin and kanamycin, and cultured at 30° C. for 8 h in a 125-mL Erlenmeyer flask (medium volume 5 mL, containing 0.3 g of $CaCO_3$) at 240 rpm. IPTG was then added to a final concentration of 0.3 mM, and the fermentation was continued for 27 h and then stopped. The final yields of valine and isoleucine were 1.26 g/L and 1.27 g/L, respectively.

The method for producing isoleucine by using threonine culture medium provided herein can be realized by those skilled in the art by improving the process parameters appropriately in view of the disclosure herein. It is specifically noted that all such substitutions and modifications will be apparent to those skilled in the art and are intended to be included herein. The method and use of the present disclosure has been described by preferred embodiments. It will be apparent to those skilled in the art that the method and use disclosed herein can be modified or appropriately changed and combined to implement and apply the techniques of the present disclosure without departing from the teachings, spirit and scope of the present disclosure. The culture media, reagents and materials using in the present disclosure are all commercially available products and can be purchased in the market. It should be noted that certain improvements and embellishments can be made by those skilled in the art without departing from the principle of the present disclosure, and should also be construed as within the scope of the present disclosure.

The invention claimed is:

1. A method for producing L-isoleucine by fermentation, comprising:

a) constructing a genetically engineered strain by transforming a host strain with a plasmid combination of pZA-ilvAIH and pZE-ilvCmD-ilvE-ygaZH;

b) culturing the genetically engineered *Escherichia coli* strain in a fermentation medium;

c) feeding threonine to the fermentation medium in a fed-batch manner, wherein the total amount of threonine added is 0.1% to 5% to produce L-isoleucine; and d) recovering L-isoleucine from the fermentation medium, wherein said genetically engineered strain comprises:

i) a feedback-resistant ilvA gene encoding a threonine deaminase that is substantially released from feedback inhibition by L-isoleucine;

ii) a feedback-resistant ilvIH gene encoding an acetohydroxy acid synthase Ill that is substantially released from feedback inhibition by L-isoleucine;

iii) a mutant acetohydroxy acid reductoisomerase gene (ilvCm), wherein said mutant acetohydroxy acid reductoisomerase gene encodes an enzyme utilizing NADH as a cofactor;

iv) a dihydroxy-acid dehydratase gene (ilvD);

v) a branched-chain amino acid aminotransferase gene (ilvE); and vi) a branched-chain amino acid exporter gene (ygaZH), wherein, in step a), said host strain is an *E. coli* strain having deletions of IdhA, pta, poxB, adhE, pflB, mgsA, frdA, dadA, avtA, and ilvE genes, said plasmid pZA-ilvAIH is obtained by ligating the feedback-resistant ilvA gene and the feedback-resistant ilvIH gene into plasmid pZAlac; and said plasmid pZE-ilvCmD-ilvE-ygaZH is obtained by ligating ilvCm, ilvD, ilvE, and ygaZH genes into plasmid pZElac.

2. The method according to claim 1, wherein feeding threonine to the fermentation medium is performed by adding a feed medium having a concentration of threonine from 10% to 14%.

* * * * *